United States Patent
Bolla

(10) Patent No.: US 8,852,132 B2
(45) Date of Patent: Oct. 7, 2014

(54) DEVICE AND METHOD FOR ANALGESIC IMMOBILIZATION OF FRACTURED RIBS

(75) Inventor: Kalman Bolla, Neuhausen am Rheinfall (CH)

(73) Assignee: Chrisofix AG, Neuhausen am Rheinfall (CH)

( * ) Notice: Subject to any disclaimer, the term of this patent is extended or adjusted under 35 U.S.C. 154(b) by 1074 days.

(21) Appl. No.: 12/549,208

(22) Filed: Aug. 27, 2009

(65) Prior Publication Data
US 2010/0081976 A1    Apr. 1, 2010

Related U.S. Application Data

(63) Continuation-in-part of application No. 10/547,336, filed as application No. PCT/CH2004/000109 on Mar. 1, 2004, now abandoned.

(30) Foreign Application Priority Data

Mar. 3, 2003   (CH) .......................................... 328/03

(51) Int. Cl.
*A61F 5/00* (2006.01)
*A61F 5/03* (2006.01)
*A61F 5/058* (2006.01)

(52) U.S. Cl.
CPC .. *A61F 5/03* (2013.01); *A61F 5/058* (2013.01)
USPC ................................................ 602/19; 602/5

(58) Field of Classification Search
USPC ........ 602/19, 5, 6, 60, 61, 32, 36, 39; 601/41, 601/44
See application file for complete search history.

(56) References Cited

U.S. PATENT DOCUMENTS

| 3,683,655 | A | * | 8/1972 | White et al. .................... 601/44 |
| 3,686,655 | A | * | 8/1972 | Kasahara ...................... 340/634 |
| 4,390,520 | A | * | 6/1983 | Nagai et al. .................. 424/449 |
| 4,600,618 | A | | 7/1986 | Raychok, Jr. et al. |
| 4,852,556 | A | | 8/1989 | Groiso |
| 6,039,706 | A | * | 3/2000 | Bolla et al. ........................ 602/5 |
| 6,516,804 | B1 | | 2/2003 | Hoffman |
| 6,602,214 | B2 | | 8/2003 | Heinz et al. |
| 6,716,186 | B1 | * | 4/2004 | Singh et al. .................... 602/22 |
| 6,971,995 | B2 | * | 12/2005 | Rolnick et al. ................. 602/12 |

FOREIGN PATENT DOCUMENTS

WO    WO 89/05620    6/1989

* cited by examiner

*Primary Examiner* — Victoria J Hicks
(74) *Attorney, Agent, or Firm* — Young & Thompson

(57) ABSTRACT

A device (22) for analgesic immobilization in the event of thorax or rib fractures as well as a method for application of such a device are disclosed. The immobilization device (22) includes a flat splint element (24) which covers a large area of the region of the break (19), and is provided with an adhesive layer (26) which is located on the side thereof facing the body and is used to adhere the immobilization device (22) to the body. In a preferred method of application, two separate areas of adhesive are applied to the patient's skin over the fracture at two different points in the breathing cycle. This allows the device to remain in place more securely under the dynamic condition of the ribcage that results from constant inhalation and exhalation.

3 Claims, 4 Drawing Sheets

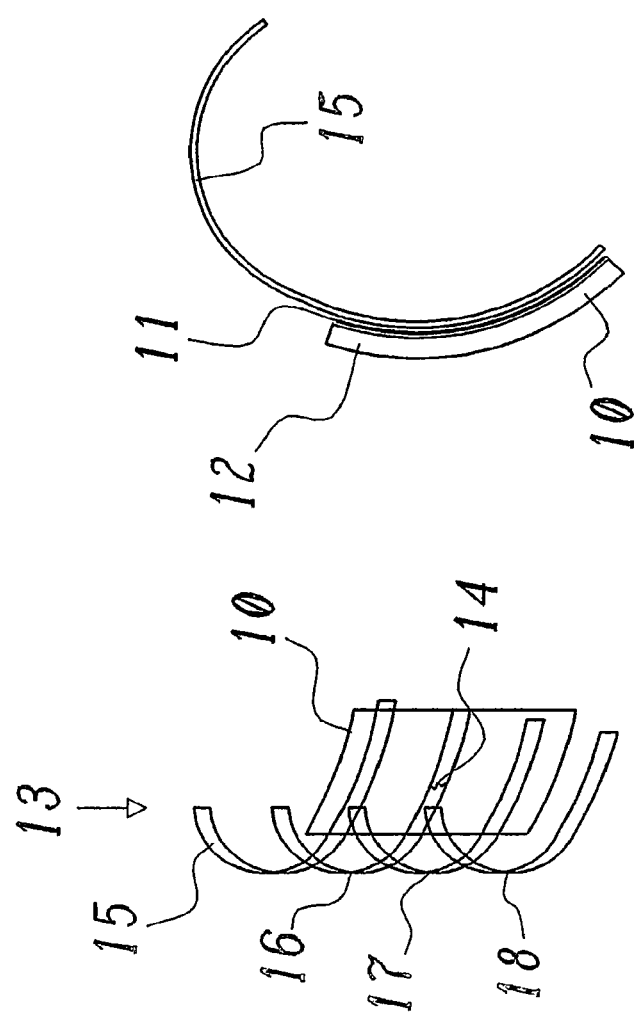

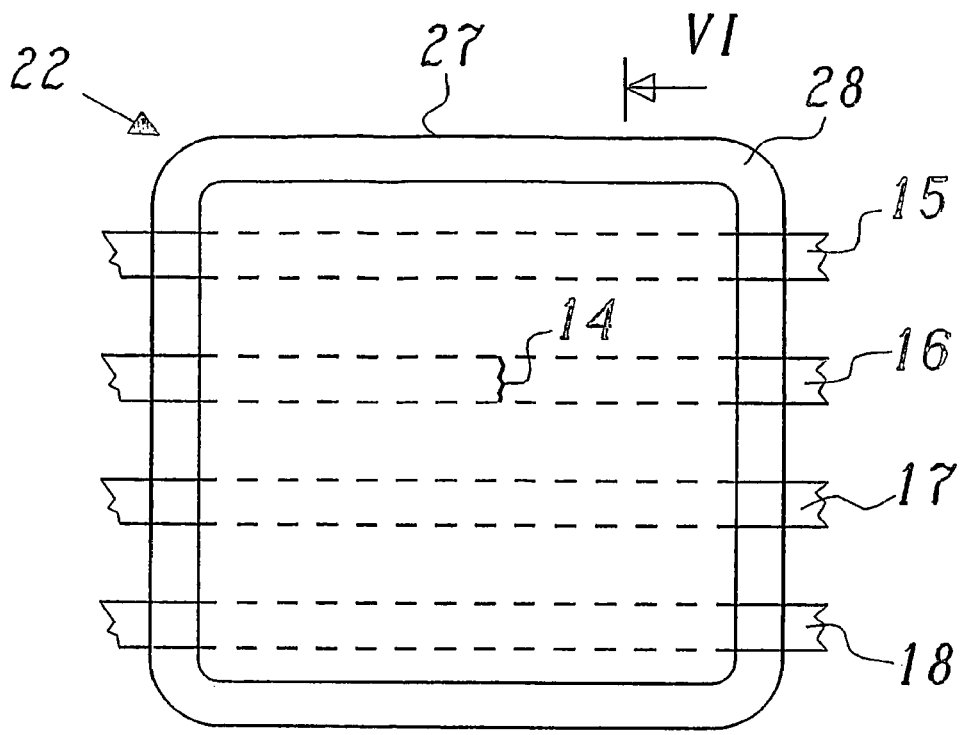
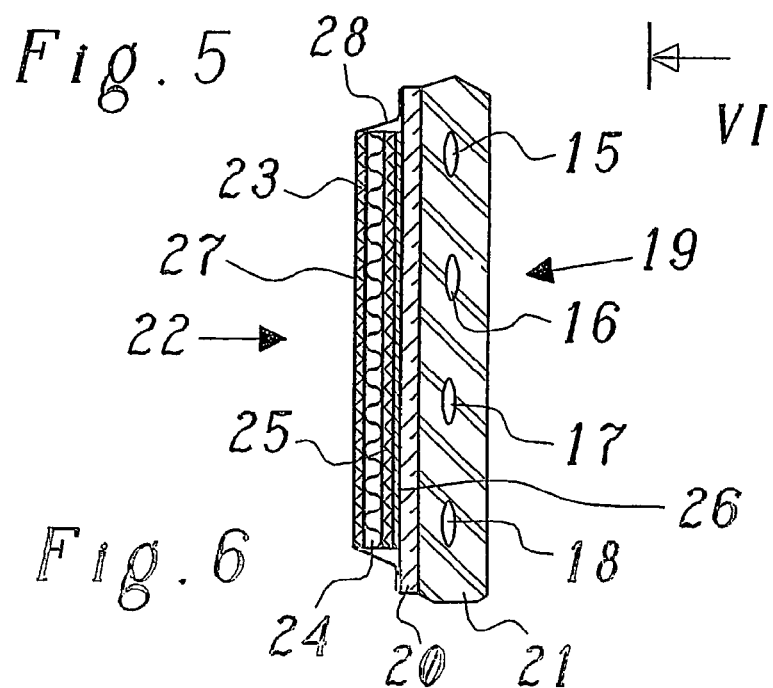

DEVICE AND METHOD FOR ANALGESIC IMMOBILIZATION OF FRACTURED RIBS

This application is a continuation-in-part of application Ser. No. 10/547,336 filed on Sep. 1, 2004; which is the 35 U.S.C. 371 national stage of International application PCT/CH2004/000109 filed on Mar. 1, 2004; which claimed priority to Switzerland application 328/03 filed Mar. 3, 2003. The entire contents of each of the above-identified applications are hereby incorporated by reference.

TECHNICAL FIELD

The present invention relates to the field of medical aids. It includes both a device and method for analgesic immobilization of fractured ribs (thorax immobilization device).

Such a device is known from, e.g., U.S. Pat. No. 4,312,334.

BACKGROUND ART

Rib fractures are very painful, especially if multiple ribs are fractured simultaneously. This is especially true while breathing, and as a result the patient tends to breathe flatly (reduced forced vital capacity, FVC), or, in case of multiple fractures on the same rib, forcing the patient to breath in an unusual way, in which the chest parts participating in breathing move in the opposite direction as usual. In most rib fracture cases, no surgical intervention is performed, and natural healing occurs. It is desirable to administer some medicine for controlling the pain of the patient in order to achieve better breathing.

The immobilization of fractured ribs presents an unique splinting challenge due to their localization. Proper splinting technique teaches that a splint should extend to include the joint on either side of the injury. Applying this general rule to the case of rib fractures would mean a circumferential brace or belt which wraps around the body. This technique was introduced by Malgaine (1859), however it is medically rather contraindicated today. This is because—due to the inhibition of the breathing—the risk of pneumonia is greatly increased in such cases. The various trials after Malgaine with taping or surgical approaches were all failures, owing to either a lack of any therapeutic advantage or the costs (e.g., with surgical approaches).

In the fact, the target of splinting is an immobilized limb in the classic bone fracture case. This lies in stark contrast to a chest injury, in which body part that moves steadily and three-dimensionally has to be splinted. In this regard, it is worth noting that the average human performs about 20,000 breathing cycles per day! This substantial difference has made it impossible even for experts to apply the results or observations of the usual splinting techniques the splinting of a rib fracture.

On one hand, a rib splint must be wide-based and must over-bridge the fracture region. As noted above, circular bandaging cannot be used without inhibiting the breathing capacity. On the other hand, the larger the splint, the stronger the forces exerted by each breathing cycle to diminish the effect of the adhesive at its periphery. The whole splint has to be rigid (and also formable at the same time) to reduce all the forces resulting from the different movements of the ribs. However, an appropriate degree of flexibility of the material may also be desirable for the patient's comfort. No known arrangement complies with these criteria before the present device and method.

It has already been known for a long time that for immobilizing fractured ribs, the side with the fracture in the thorax can be fixed by an adhesive plaster, in order to reduce the movement of the fractured rib. However, this is usually not sufficient. There is a suggestion (GB-A-624,425) to use bundle-like, stretchable stripes instead of the plaster, which can be prestreched by means of a releasable stretching device. However, those immobilizing devices ensure a limited mobility in the region of the fracture, but, at the same time, they hinder breathing to a large extent, as well.

The earlier mentioned description U.S. Pat. No. 4,312,334 suggests binding a frame around the patient. The front side of the frame consists of two vertical, arched supporting elements over the chest. The indented part of the thorax in the fracture area is drawn out by means of a wire fixed on its one end to the chest and on the other end to the supporting element. In this way, the fractured ribs can be kept in a position suitable for healing, easing the pain that reduces breathing.

The drawbacks of this arrangement include the necessary intervention, the difficulty in positioning the wire, and the hindering of the patient's movements by the stretched wire and the frame.

Shippert (1980; U.S. Pat. No. 4,213,452) describes a "compound" splint, primarily for use after nasal surgery. The splint is put together on the patient. Adhesive tapes are used as a basic layer for securing a secondary component followed by a malleable metal sheet and the closing layer(s). This reference makes no suggestion of possible use in rib fracture, and in fact concerns itself only with a small and immobilized area. It is entirely unsuitable for use in connection with a larger and moving area, such as the chest.

Groiso (1986; U.S. Pat. No. 4,852,556) describes an orthopedic rigid splint-plate orthesis of different sizes and forms depending on the target of the immobilization. One of the claimed targets is a rib fracture. The material used requires a curing process, and any mention of an adhesive in such reference is proposed only in connection with such curing period. Groiso acknowledges that for securing a bigger thermoplastic splint, adhesive attachment is not sufficient. Accordingly, he uses a circumferential wrapping around the body. In fact, the possible positive effect of his method is based on the circular bandaging of the thorax, a technique used since the middle of the nineteenth century.

Erickson (WO-A1-89/05620) provides a fixing plate for rib fractures being flexurally rigid in the longitudinal direction, and to a certain extent flexible in the direction perpendicular to this. In addition, it is to a certain extent also rotatable in the diagonal direction (being able to torsion). This arrangement serves for supporting and fixing the individual fractured ribs on the one hand, and at the same time, should make free breathing movement of the patient possible, on the other hand. This objective is achieved by using a plate made of a flexible, elastic material, such as rubber or plastic, in which several closed, long-shaped cavities parallel to the longitudinal, flexurally rigid direction are arranged. In each of these cavities, freely movable, as one-dimensional splint elements, rods made of an inelastic but deformable material are arranged. In case of a rib fracture, due to their deformability, these splints can be fitted to the contour of the rib. The plate with the splints will be stuck flat to the chest, in this position the splints run parallel to the ribs. Thus, the ribs are fixed in the longitudinal direction, whereas at normal breathing, the chest is able to expand without hindrance.

Though the one-dimensional splints fix the fractured ribs in the longitudinal direction, they allow for unhindered movement of the ribs relative to each other for breathing. This is partly due to the free movability of the splints in the cavities. Due to this movability of the ribs relative to each other during breathing, the distances between individual ribs change. As a result, the fractured sites of the ribs may rub on each other, causing pain for the patient. This pain may lead to a cramp in the intercostal musculature, which only exacerbates the pain.

Bolla et. al. (1996; U.S. Pat. No. 6,039,706) describes a medical splint, metal sheets for such a splint, and its use for securing and immobilizing movable body parts in particular extremities. The specially prepared material ensured "a high shapability and stiffness at the same time." It is rigid and formable at the same time, a ready-to-use splinting material without the necessity of a curing process. This reference proposes the device for use only for conventional (e.g., limb) splinting. Splinting of the thorax (rib fracture) is not suggested as appropriate for such device. The breathing-related, nearly continuous movement of the thorax excludes such an application without a belt.

Singh et. al. (2000; U.S. Pat. No. 6,716,186 B1) describes curable adhesive splints and methods. The splints include at least a curable splinting layer (developing the requested stiffness) and an adhesive one. The declared target of the splinting is "Immobilization of smaller skeletal features, such as fingers or of oddly shaped skeletal features, such as noses . . . ." The use of the claimed technique for ribs is not mentioned. The inventors seemingly knew the substantial differences in the requirements between splinting an immobilized body part and a steadily moving one, such as the thorax. The device described in this patent could only be used in connection with a rib fracture (if at all) with an additional belt. This, however, is already the subject of the Groiso reference described above (1986; U.S. Pat. No. 4,852,556). The securing of the splint position with an adhesive layer, as Groiso describes, can be utilized for larger splints only with the additional wrapping necessitated thereby. He secures the rib splint from similar materials, with an adhesive used only during the curing process.

Rolnik et. al. (2004; U.S. Pat. No. 6,971,995) proposes an adhesive elastic splint construction for the treatment of rib injuries. He even disclaims the applying of an inelastic adherent patch even because it is asserted not to be appropriate for allowing the patient's comfort.

SUMMARY OF THE INVENTION

Based on the above, the task of the present invention is to create an analgesic immobilizing device for use in thorax fractures eliminating the drawbacks of the devices known, with a device that is simple to produce, easy to apply, quite safe to use and whose use results in a reduction of pain and improvement of breathing, without influencing significantly the free movement of the patient's chest.

It is proposed at the first time an adhesive, rigid, and yet formable splint for the treatment of rib fracture. The rigidity ensures the desired partial immobilization of the thorax, while the formability makes wearing of the splint comfortable for the patient and reduces the forces acting against the adhesive during breathing. To compensate, or at least reduce the effect of the forces occurring by each breath increasingly on the adhesive at the periphery of the splint, the fixation with the inherent adhesive layer is strengthened with a non rigid protective foil, which is larger than the splint element. The two fixations must be performed in two steps in different phases of the breathing cycle. The two-step fixation makes the use of a belt unnecessary.

The task is solved according to features described in further detail below and in the attached claims. The essence of the invention lies in a formable, flat splint element being rigid in itself covering the fracture area, including the fractured rib(s) and the neighboring, non-fractured ribs as well, which splint is provided with an adhesive layer on its side facing the body suitable for adhering the immobilizing device to the body. The splint element should be adhered to the fractured part of the thorax (fracture area) so that preferably the neighboring, non-fractured parts are also covered. The fractured ribs will thus be secured by the splint element being relatively rigid in itself, while nevertheless being formable at the same time, and is supported also by the uninjured ribs. This stabilization leads to reducing the pain and consequently improves the patient's breathing.

In a preferred embodiment of the invention the splint element can be fitted to the outside contour of the thorax particularly without any additional aid or tool, whereas it preferably contains a deformable plastic plate or a plastically deformable metal plate. This plate increases further the efficiency of the splint and makes its application simpler.

The plastically deformable metal plate is made preferably of aluminium, where the plastically deformable metal plate is corrugated in order to improve local deformability with increasing at the same time the rigidity, and the crests of corrugations of the plate are essentially parallel to the ribs to be treated. Such a splint material has already successful applications for different purposes (WO-A1-97/22312 resp. U.S. Pat. No. 6,039,706).

The wear of such a splint element can be made more comfortable so that the upper and/or lower side of the splint element is provided with a covering, made preferably of some tissue, or of an elastic foam material. In addition, some perforation can also be made in the splint element in order to achieve better permeability of the immobilizing device.

In order to protect the immobilizing device against external effects, such as water or similar substances, it is preferable to use a protecting foil for covering the upper side of the splint element. This protecting foil should be adhered onto the splint element and also to the chest after applying the splint on the body. A protection of the sides can also be achieved easily so that the foil over the splint element sticks out on the sides, and forms a continuous rimstrip, whereas the lower side of the protecting foil is also provided with an adhesive layer in the field of the rimstrip.

In order to reduce further the pain caused by rib fractures it is preferred if the immobilizing device is provided additionally also with some local analgesic substance. For this purpose, pain killers may be contained in a smaller pad or cushion coupled to the immobilizing device by a releasable bond. Another possibility is that parts of or the total of the adhesive layer contains a pain killer.

BRIEF DESCRIPTION OF THE FIGURES

The invention will be explained on the basis of figures showing some embodiments.

FIG. 1 illustrates a very simplified perspective view of a first embodiment of the immobilizing device of the invention for putting to rest position the injured ribs, FIG. 2 shows a top view of the immobilizing device shown in FIG. 1, FIG. 5 is a top view from the front of a second embodiment of the invention showing the immobilizing device adhered to the rib fracture shown in FIG. 3, FIG. 6 illustrates the effect of the adhered immobilizing device in a view similar to that in FIG. 4.

DETAILED DESCRIPTION OF THE INVENTION

Figure 3:
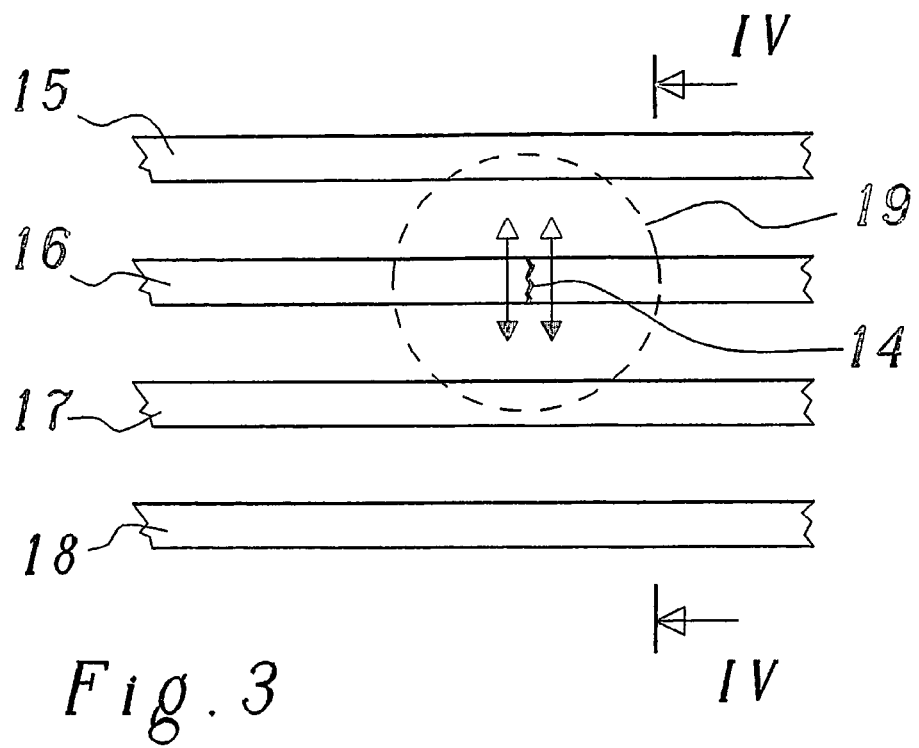
FIG. 3 is a top view from the front of an example of rib fracture showing four ribs from among which the second from the top is fractured.

The device according to the invention is applied to fractured ribs (thorax fractures). In these cases the object is to reduce the movement of the injured ribs in the chest.

An embodiment of such an immobilizing device and its application are shown in a significantly simplified way in FIGS. 1 and 2. FIG. 1 shows the scheme of four ribs 15-18 from one side of a chest 13, from among which the second rib from the top, rib 16 has a fracture 14. The tissue and skin layers of the body over ribs 15-18 are not shown for simplicity reasons. The intercostal musculature is not shown either. A flat, splint-like immobilizing device 10 fitted to the arching of chest 13 is adhered to the area of chest 13 surrounding fracture 14, on a large part of the total surface. The main component of the immobilizing device 10 consists of a splint element 12 (FIG. 2) in form of a plate made of a suitably rigid, but at the same time plastically deformable, material. Adhering is achieved by applying an appropriate adhesive layer 11 on the inside of splint element 12, similarly to plasters (FIG. 2). The size (lateral dimension) of the immobilizing device 10 is chosen preferably so that the immobilizing device 10 covers not only the injured rib 16, but also the neighboring ribs 15 and 17 in a sufficient manner.

Through adhering, the immobilizing device 10 is supported by the not fractured part of the injured rib(s) and by the uninjured neighboring ribs 15 and 17 and keeps the fractured rib 16 in a fixed position relative to the neighboring ribs 15 and 17. This hinders to a great extent any painful movement of the injured rib 16 at breathing, coughing, laughing or in other similar situations eliminating or at least reducing thereby the pain caused by these movements.

Additionally, some means can also be applied locally to the inside of the immobilizing device 10 for reducing the pain caused by the injured rib 16. Preferably pads or cushions impregnated with some analgesic material having its effect through the skin are used, which are connected to the inside of immobilizing device 10 by a releasable bond, e.g. by adhering or by hook and loop fastener. Another solution may be to impregnate parts of or the total adhesive layer 11 with a suitable pain killer.

Figure 4:
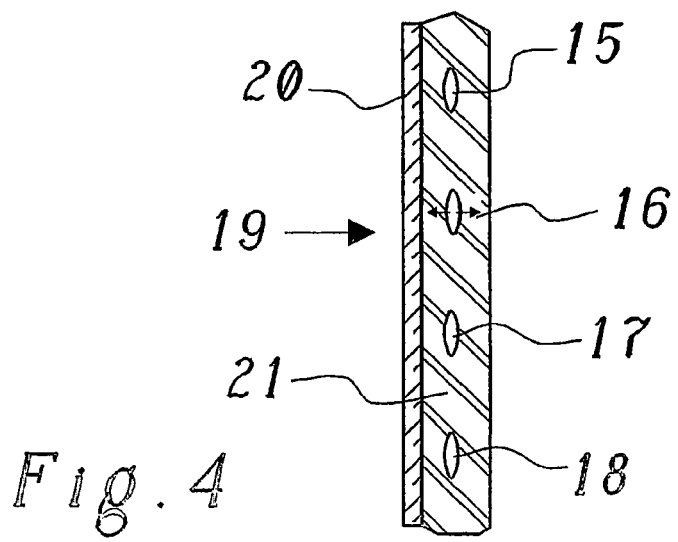
FIG. 4 shows the rib fracture in FIG. 3 in a simplified section along the line IV-IV with the fracture area.

The effect of the immobilizing device 10 according to the present invention may be explained on the basis of FIGS. 3-6. In this case, we also have four parallel ribs 15-18, from among which the second one from the top, rib 16 has a fracture 14 (of course, it is also possible that more fractured ribs are present). Considering the section of the chest along the line IV-IV in FIG. 3, the configuration shown in FIG. 4 is obtained in a simplified form. Ribs 15-18 are embedded into intercostal musculature 21 serving, among other things, for breathing. This is covered by a multilayer consisting of skin and fat tissues which, in a simplified way, can be denoted as a skin/fat tissue layer 20. In the area of fracture (fracture area 19), the fractured rib 16 looses at least in part its stability, and as a result, a frictional movement(marked in FIGS. 3 and 4 by double arrows) of the ends of the fracture relatively to each other may occur causing significant pain to the patient at any movement of the chest.

If, according to FIGS. 5 and 6 a flat immobilizing device 22 is adhered to fracture area 19 involving rib 16 and preferably to the not injured ribs 15, 17 and 18 as well, fracture area 19 is stabilized so that rib 16 is immobilized in se and also relative to the other ribs 15, 17 and 18. This leads to a less painful breathing of the patient improving thereby the way of his/her breathing, as well.

Clinical experiments were carried out in 90 patients (72 of them using the immobilizing device, 18 being in the control group) which patients had fractures up to 5 neighboring ribs, in which experiments the intensity of pain was determined by an analogous scale before the admission of the patients to the study, and 1-2, 24, 48 and 72 hours after that. In comparing with the control group, the intensity of pain in rest ($p<0,05$), and especially at forced inspiration ($p<0,01$) was over the whole period significantly less than in the control patients. The reduction of pain owing to the use of immobilizing devices 10 or 22 was measurable already even 1 hour after putting them on, whereas the control patients experienced a measurable reduction of pain only after 2-3 days.

Spirometric measurements were carried out in 29 patients before, and 1-2, 24, 48 and 72 hours after the adhering of the immobilizing device (in several patients in all these periods). Two different sizes of immobilizing devices (12×17 cm and 17×17 cm) were used according to the size of the fracture area. In 12 further patients (control patients) was the fracture area covered only by operation pads. In these control patients the forced vital capacity (FVC) hindered by the fracture, was further reduced by 174 ml in the average after 1-2 hours, and improved within further 24 or 48 hours only by 4 or 34 ml. To the contrary, in patients treated with the immobilizing device, the FVC continuously and significantly improved ($p<0.001$), by 153 ml in the average already after 1-2 hours, and by 384, 474 and 616 ml after 24, 48 and 72 hours, after the application of the immobilizing device, respectively. Just like FVC, the spirometric parameters FEV1, IVC and PEF improved also by using the immobilizing device.

Figure 7:
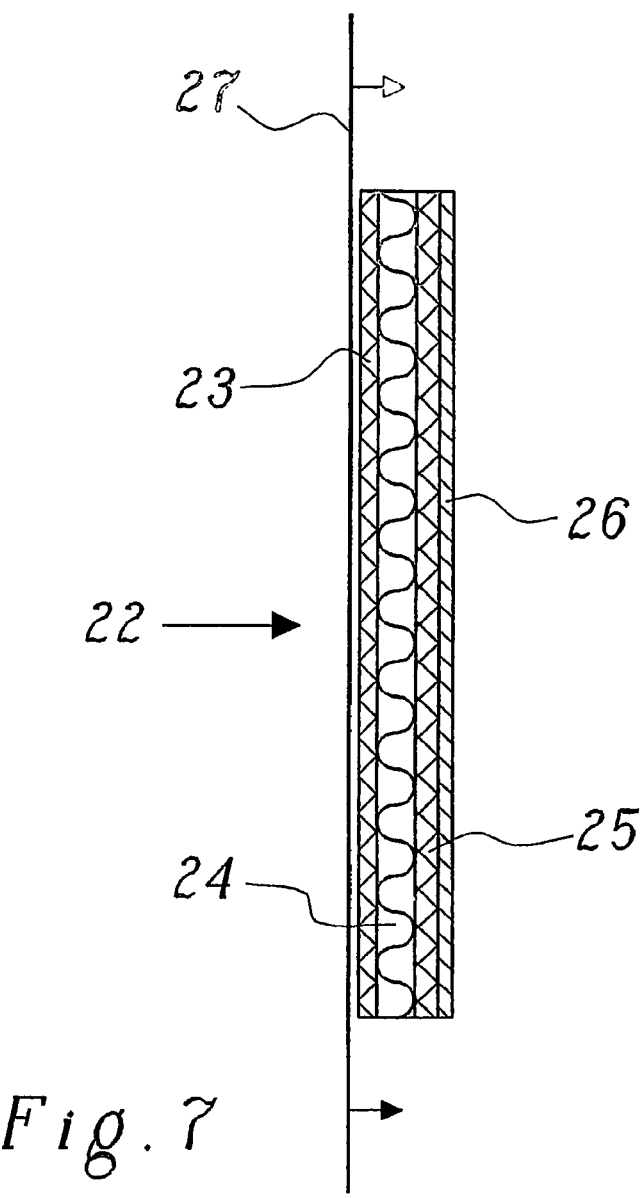
FIG. 7 shows an enlarged view of a section through the immobilizing device shown in FIGS. 5 and 6.

A preferred embodiment of immobilizing device 22 is shown in FIGS. 5-7. The immobilizing device 22 comprises a flat splint element 24 as central component, in the present case made of a corrugated aluminum plate. The thickness and corrugation of the plate are chosen so that splint element 24 may be fitted easily to the area of the fracture to be treated in the arching of the chest by bare hands without any additional aid, and on the other hand, it is appropriately rigid for its function as support and immobilizing means for the fracture. Splint elements described in WO-A1-97/22312 are also suitable for this purpose (this is why the dates about the material used in that description are taken over in the present application).

In order to fit immobilizing device 22 best to the chest, the crests of the corrugations of splint element 24 are arranged parallel to the ribs. Splint element 24 is provided with a covering 25 on its lower side and covering 23 on its upper side for making its wearing more comfortable. Coverings 23 and 25 are preferably made of an elastic, foamed open-pored or perforated plastic material. Covering 25 at the lower side is provided with an adhesive layer 26 on its outer surface, by means of which the immobilizing device 22 can be adhered to the fracture area. As adhesive materials for the adhesive layer, every adhesive suitable for medical applications can be used. During application, the upper side of the immobilizing device 22, e.g. the outer surface of covering 23 is adhered to a protecting foil 27 which is greater on the sides than the covering, thus forming a protruding rim 28 (FIG. 5). If the protecting foil 27 with its protruding rim 28 is adhered to the skin of the patient, immobilizing device 22 is protected against external effects, thus the patient can e.g. take a shower without any negative consequence. The protecting foil is permeable for air (so called breathing foil) and water-tight. Splint elements 24 in the present invention may be made of other materials than corrugated aluminum plate, such as plastic plates or similar materials being rigid enough and at the same time, sufficiently plastically deformable. Splint element 24 is preferably provided with holes, e.g. in form of a perforation, in order to be permeable and being more comfortable to wear.

The inventor has also discovered that the present device offers a further improvement over any known prior art in the field of analgesic relief for rib fractures. As described in detail above the present device is preferably constructed with two adhesive areas. One of these areas is that of adhesive layer 26. The other is that of the perimeter area of protecting foil 28. In at least one embodiment, the adhesive layer 26 is surrounded by the perimeter adhesive area of layer 28. The perimeter area of protecting foil 28 is adhered to the skin of the chest in a separate step from that of adhering adhesive layer 26.

As described above, one of the beneficial effects of the perimeter adhesive area of layer 28 is to act as a barrier to things such as water. The presence of this layer allows the patient to engage in activities such as showering without adverse effect to the device.

The combination of these two separate adhesives has proven to have yet another, entirely different advantage, however.

One of the characteristics of rib fractures that makes their treatment considerably more difficult than fractures of other bones is the necessarily dynamic nature of ribs. By their very nature, ribs must be in nearly constant motion with respect to the remainder of the skeletal structure. The inhalation and exhalation of air required for breathing is, at its core, a fundamental mechanical operation.

Like a bellows, the lungs must be expanded and contracted to draw in oxygen-rich air in and expel the carbon dioxide produced by the respiration process. It is the skeletal-muscular structure of the ribcage that acts as the bellows.

Given this crucial function, a fractured rib or ribs cannot be rigidly fixed in place by a cast or other similar immobilizing device. To draw a contrast with the leg, as an example, the two elements of a fractured tibia can be set back into proper relationship with one another and then rigidly fixed in place by a cast or other immobilizing device. Such a cast can not only surround the lower part of the leg, but can extend down past the ankle. In so doing, such a cast holds several bones of the leg and foot in a fixed positional relationship with one another. While uncomfortable, this does not interfere with the overall health of the patient. It is only the activities of mobility that are affected while the cast is in place.

It is not, however, possible to hold the chest in place in a similar manner. To do so would bring to a halt the motion necessary for inhalation and exhalation, with obvious disastrous consequences.

While the present device makes a considerable advance in the possibilities for treatment of rib fractures by virtue of its ability to be secured to that area of the skin of a patient that overlies the fracture or fractures, the presence of the two different adhesive areas offers yet another considerable advance in treatment, insofar as it allows for yet further accommodation of the different positions that the ribcage must occupy during maximum and minimum lung volume at different times of the breathing cycle.

With this in mind, it has been discovered that considerable gains can be achieved by adhering the two different adhesive portions at two different point in the breathing cycle. Under one example, the adhesive portion 26 is first adhered to the skin that overlies the fracture or fractures when the patient is in a condition of minimum lung volume, namely when the patient has finished exhaling, or very nearly so. The other adhesive portion 28 of the perimeter is not attached to the surrounding skin at the same time, however. Instead, the patient is instructed to inhale, and the adhesive portion 28 is then adhered when the lung volume is at or near its maximum volume.

In this way, the inner area of adhesive 26 is secured to the skin at a time when the skin is relatively slack at the end of exhalation. The outer perimeter adhesive 28 is secured to the skin when the skin when the skin is relatively stretched at the end of inhalation. Accordingly, when one of the areas of adhesive is stressed by the movement of skin (and underlying structure) away from the relationship the adhesive had with the skin at the time it was adhered, the other area of adhesive is having a corresponding stress relieved as it moves back into the relationship it had with the skin and underlying structure at the time of adhesion.

This method of application greatly improves the ability of the device to provide an overall secure relationship of the rigid portion of the device with the fractured rib or ribs during the many tens of thousands of respiration cycles that will take place from the time that the device is attached to the time that it is removed after the rib or ribs have healed.

It is also possible that the relationship of the two can be reversed, so that the inner adhesive area 26 is secured when the lungs are at or near a condition of maximum volume, and the outer adhesive is attached at or near a condition of minimum volume.

It is also unnecessary that the attachment of either adhesive portion take place at the limit of either inhalation or exhalation. So long as the two steps of adhesion take place at different points in the cycle, an advantage will be had over a corresponding method and device in which all adhesion takes place at essentially a single point in the respiration cycle.

REFERENCE NUMBERS

10, 22 immobilizing device
11 adhesive layer
12 splint element (flat)
13 chest
14 fracture
15-18 ribs
19 fracture area
20 skin/fat tissue layer
21 intercostal musculature
23 upper covering
24 splint element (flat)
25 lower covering
26 adhesive layer
27 protecting foil
28 rim (protecting foil)

The invention claimed is:

1. A method of splinting a rib fracture of a patient, comprising steps of:
    providing a device comprising:
        a single splint element that is rigid and plastically deformable, has a surface large enough to cover a region of a rib fracture including neighboring ribs, and is provided with a first adhesive on an inner surface thereof;
        a perimeter secured to the single splint element and lying outside of an outer edge of the single splint element, the perimeter having a second adhesive thereon facing in a same direction as the first adhesive; and
    applying the device to a patient by the following steps:
        1) adhering the single splint element to a first area of skin of the patient that overlies the rib fracture by contacting the first adhesive to said first area of skin, while preventing the second adhesive from contacting skin of the patient; and 2) after adhering the single splint element to the first area of skin, exposing the perimeter and adhering the perimeter to a second area of skin of the patient that lies outside of the first area of skin;

wherein step 1 is performed at a different point in a breathing cycle of the patient than step 2;

wherein the step 1 is performed when lungs of the patient are in a condition of lower volume than when step 2 is performed.

2. The method of claim 1, wherein step 1 is performed when the patient is in a condition of maximum exhalation.

3. The method of claim 2, wherein step 2 is performed when the patient is in a condition of maximum inhalation.

* * * * *